(12) United States Patent
Kim et al.

(10) Patent No.: US 11,602,539 B2
(45) Date of Patent: Mar. 14, 2023

(54) HEMOSTATIC COMPOSITION COMPRISING CROSS-LINKED HYALURONIC ACID DERIVATIVE MATRIX

(71) Applicant: BMI KOREA CO., LTD, Jeju-si (KR)

(72) Inventors: Min-Kyoung Kim, Jeju-si (KR); Koo Woo, Jeju-si (KR); Yeong Jun Baik, Seoul (KR); Kyeong Woo Min, Asan-si (KR)

(73) Assignee: BMI KOREA CO., LTD, Jeju-si (KR)

( * ) Notice: Subject to any disclaimer, the term of this patent is extended or adjusted under 35 U.S.C. 154(b) by 341 days.

(21) Appl. No.: 16/327,961

(22) PCT Filed: Sep. 6, 2017

(86) PCT No.: PCT/KR2017/009770
§ 371 (c)(1),
(2) Date: Feb. 25, 2019

(87) PCT Pub. No.: WO2018/048199
PCT Pub. Date: Mar. 15, 2018

(65) Prior Publication Data
US 2019/0201436 A1    Jul. 4, 2019

(30) Foreign Application Priority Data
Sep. 6, 2016    (KR) .................... 10-2016-0114303

(51) Int. Cl.
| | | |
|---|---|---|
| *A61K 31/728* | (2006.01) | |
| *A61K 35/583* | (2015.01) | |
| *A61K 38/48* | (2006.01) | |
| *A61P 7/04* | (2006.01) | |
| *C08B 37/08* | (2006.01) | |

(52) U.S. Cl.
CPC .......... *A61K 31/728* (2013.01); *A61K 35/583* (2013.01); *A61K 38/48* (2013.01); *A61K 38/4833* (2013.01); *A61P 7/04* (2018.01); *C08B 37/0072* (2013.01)

(58) Field of Classification Search
CPC ..... A61K 31/728; A61K 38/4833; A61P 7/04; C08B 37/0072
See application file for complete search history.

(56) References Cited

U.S. PATENT DOCUMENTS

| | | | |
|---|---|---|---|
| 7,435,425 B2 * | 10/2008 | Qian | .................. A61L 24/0031 |
| | | | 424/422 |
| 8,021,684 B2 | 9/2011 | Moller et al. | |
| 9,408,945 B2 | 8/2016 | Goessl et al. | |
| 2003/0060448 A1 | 3/2003 | Rivarossa et al. | |
| 2006/0246137 A1 | 11/2006 | Hermitte et al. | |
| 2012/0128653 A1 * | 5/2012 | Goessl | ................. A61L 24/106 |
| | | | 424/94.64 |

FOREIGN PATENT DOCUMENTS

| | | |
|---|---|---|
| CN | 101313915 | 12/2008 |
| CN | 105400214 | 3/2016 |
| JP | 2001-510713 | 8/2001 |
| JP | 2002-233542 | 8/2002 |
| JP | 2010-077434 | 4/2010 |
| JP | 2011-518780 | 6/2011 |
| JP | 2012-511548 | 5/2012 |
| JP | 2013-530955 | 8/2013 |
| JP | 2015-519152 | 7/2015 |
| KR | 10-2007-0046093 | 5/2007 |
| KR | 10-2010-0132878 | 12/2010 |
| KR | 10-1240518 | 3/2013 |
| KR | 10-2013-0121702 | 11/2013 |
| KR | 10-2014-0074992 | 6/2014 |
| KR | 10-2014-0082841 | 7/2014 |
| KR | 10-1551681 | 9/2015 |
| RU | 2360928 | 7/2009 |
| WO | 00-46253 | 8/2000 |
| WO | 2016-100861 | 6/2016 |

OTHER PUBLICATIONS

Google machine translation of CN101313915B, https://patents.google.com/patent/CN101313915B/, accessed online on Jan. 21, 2021. (Year: 2021).*
English language machine translation of KR 20100132878 A by Google Patents, https://patents.google.com/patent/, accessed online on Jun. 24, 2021. (Year: 2021).*
Miyamoto et al., Spine, 2006, 31, p. E91-E97. (Year: 2006).*
EPO, European search report of EP 17849083.5 dated Mar. 10, 2020.

* cited by examiner

*Primary Examiner* — Jonathan S Lau
(74) *Attorney, Agent, or Firm* — Lex IP Meister, PLLC

(57) ABSTRACT

The present invention relates to a hemostatic composition and a method for preparing thereof, and more specifically, relates to a hemostatic composition comprising a cross-linked hyaluronic acid derivative matrix which is suitable to be used for hemostasis and a method of preparation of such a composition.

11 Claims, 15 Drawing Sheets

[Fig. 1]
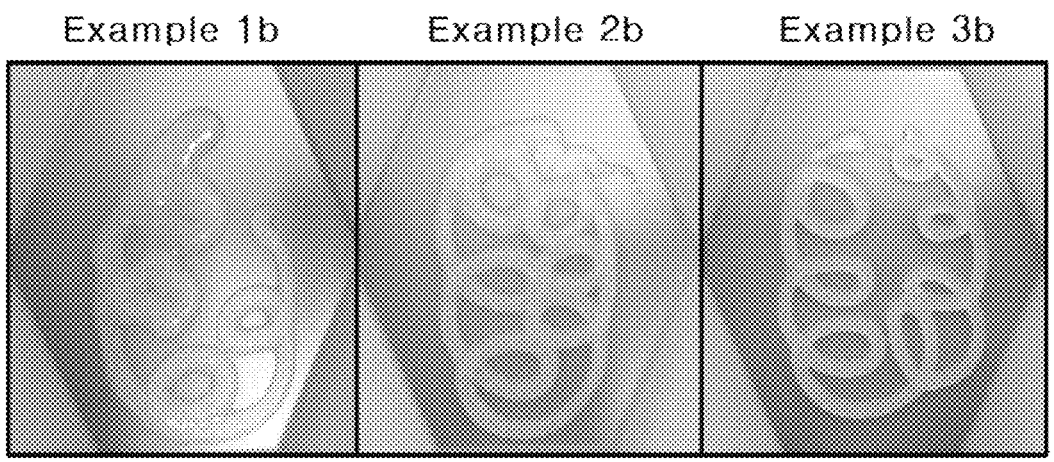

[Fig. 2]
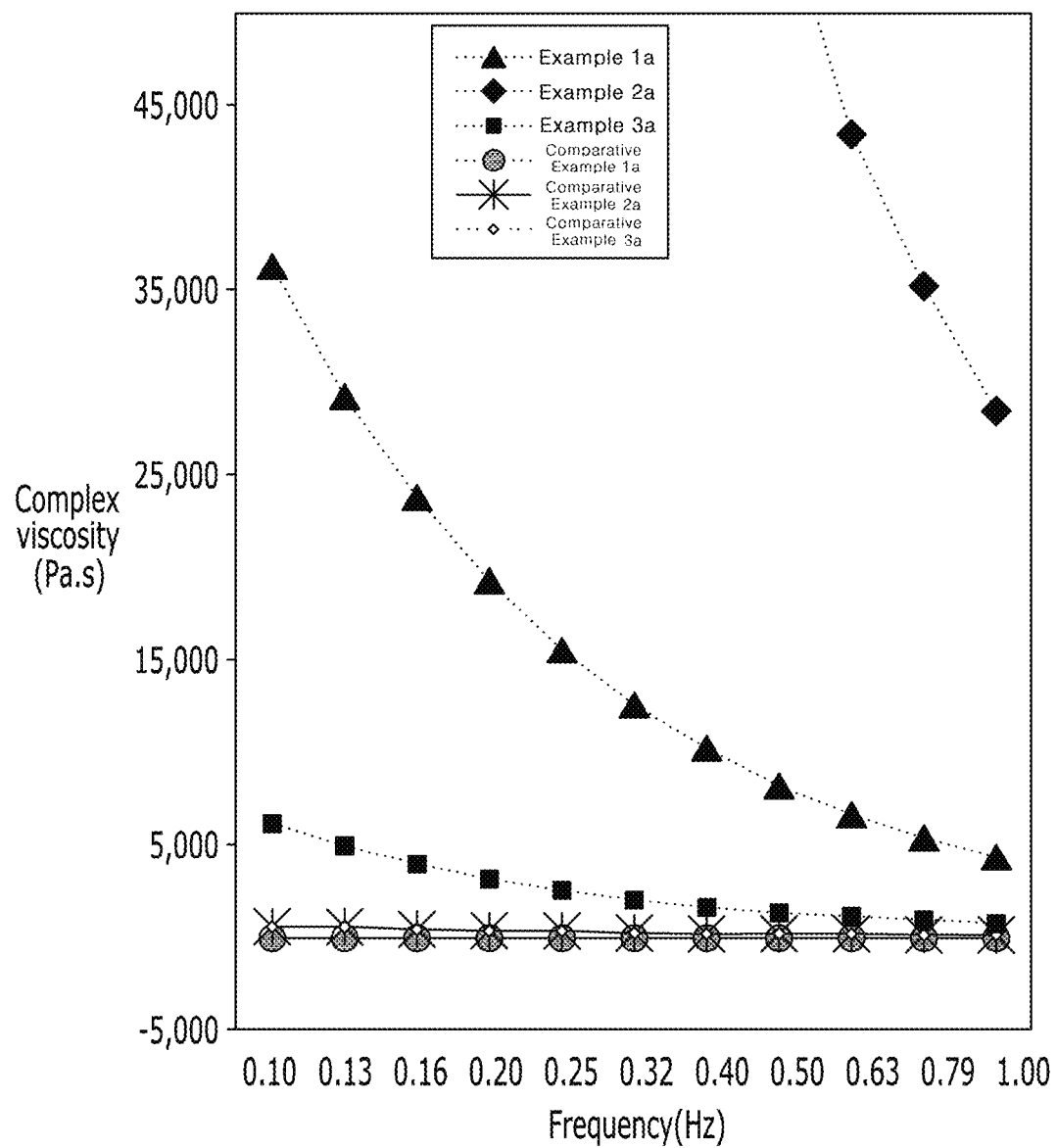

[Fig. 3]
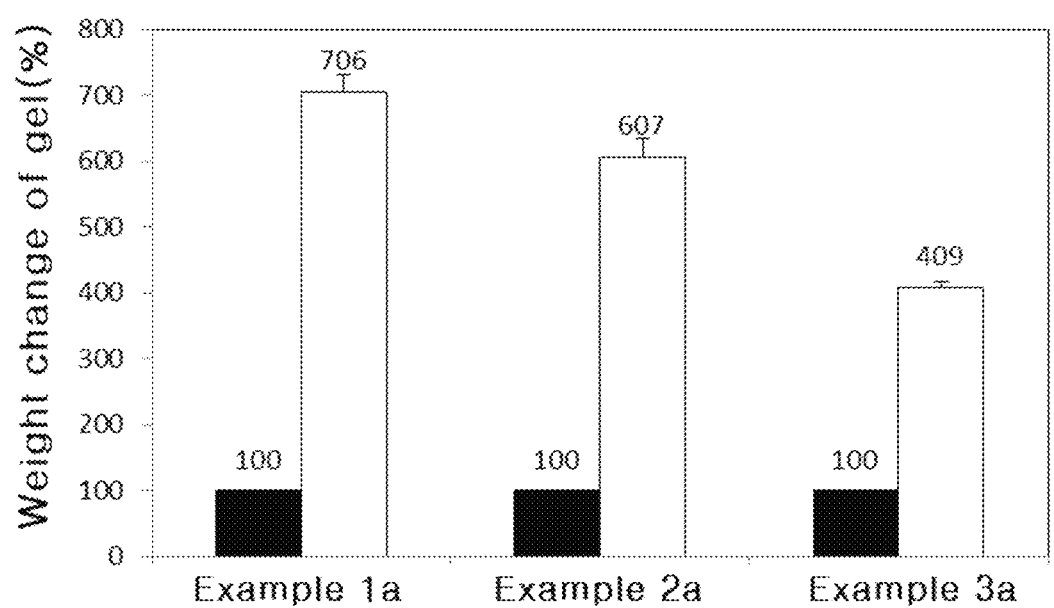

[Fig. 4]
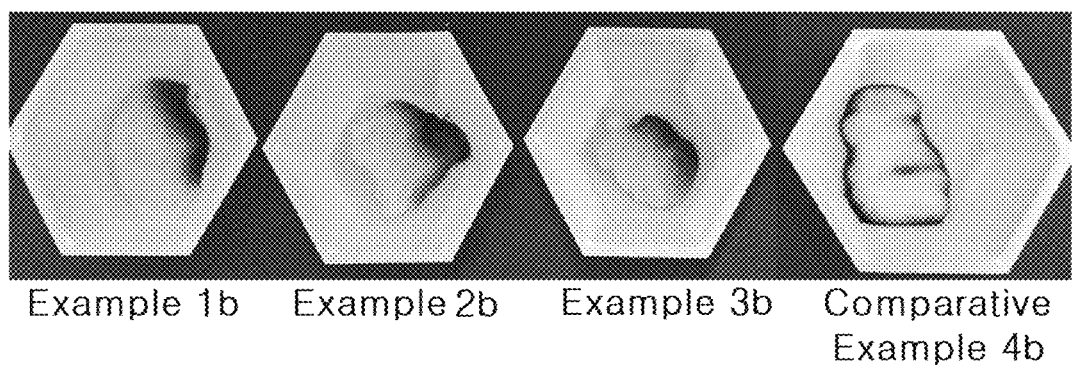
Example 1b  Example 2b  Example 3b  Comparative Example 4b

[Fig. 5a]
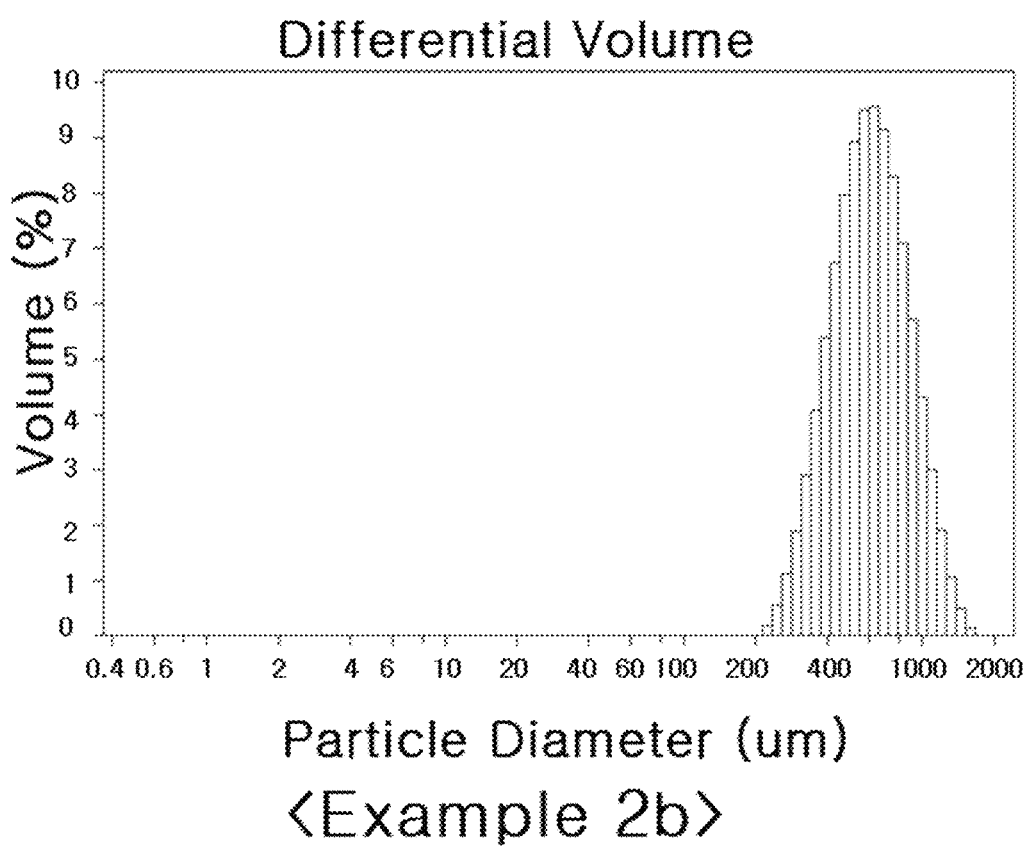
<Example 2b>

[Fig. 5b]
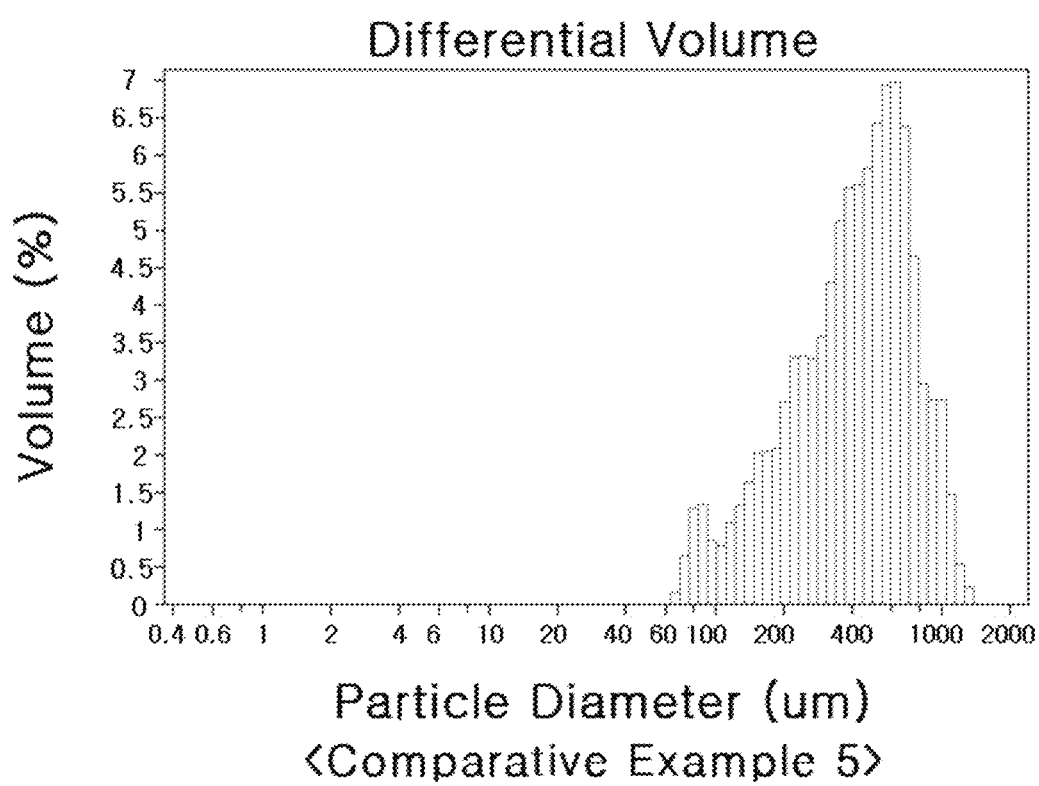

[Fig. 6a]
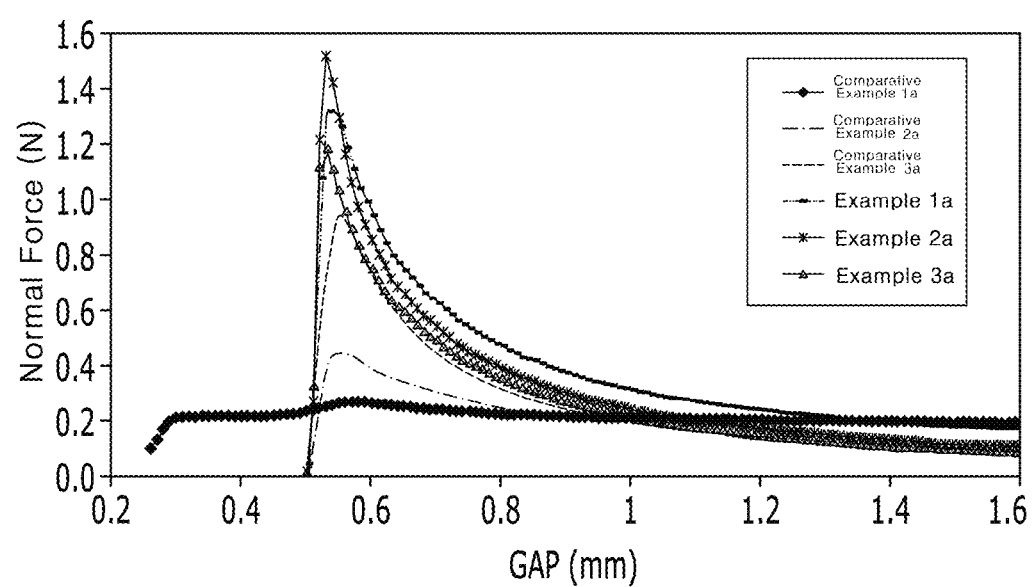

[Fig. 6b]
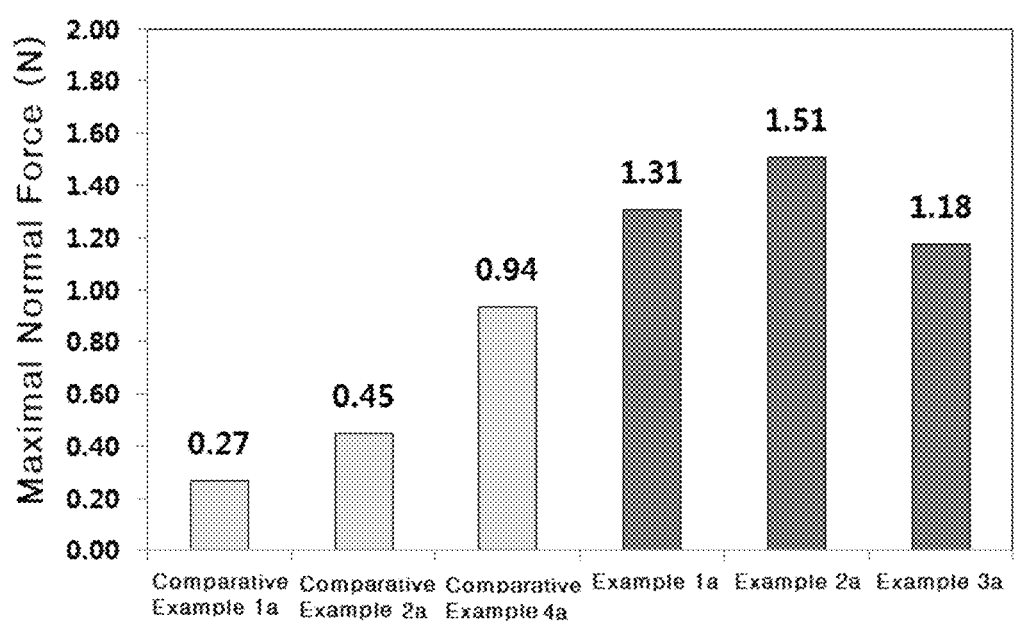

[Fig. 7a]
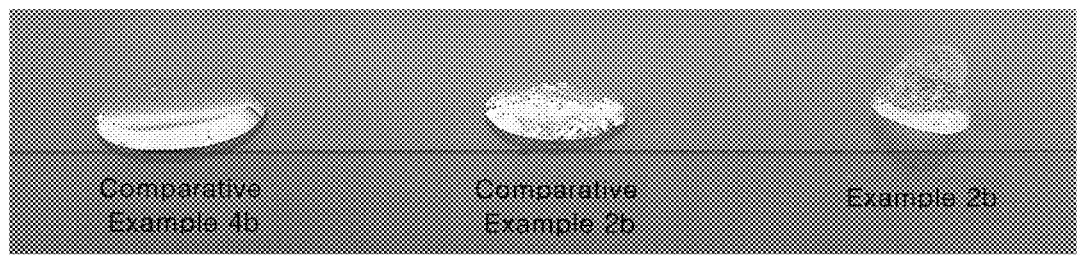

[Fig. 7b]
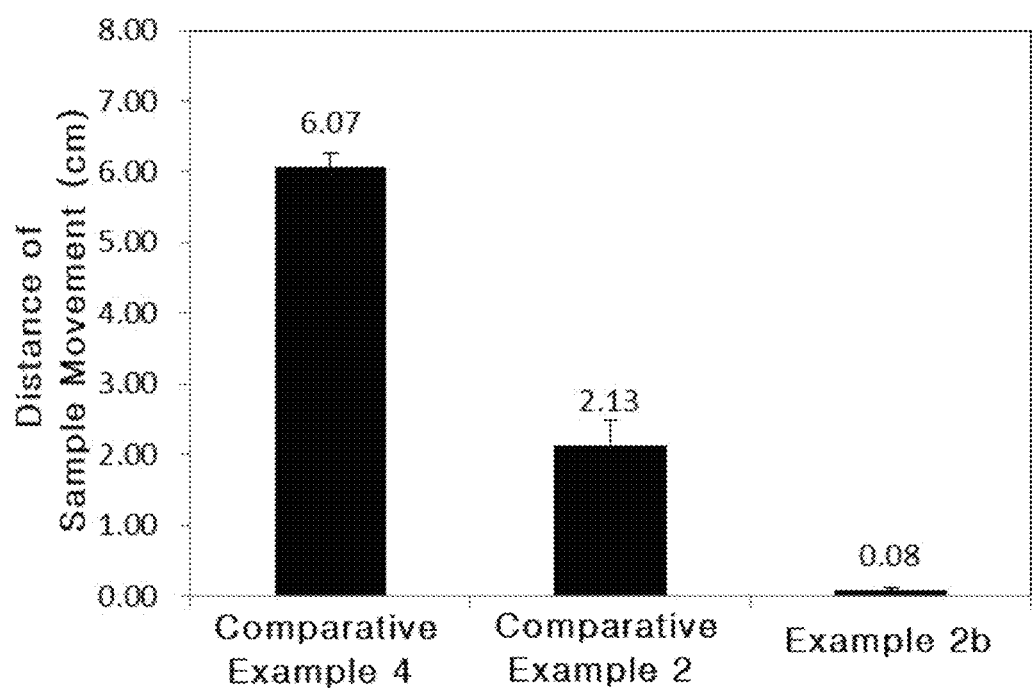

[Fig. 8]
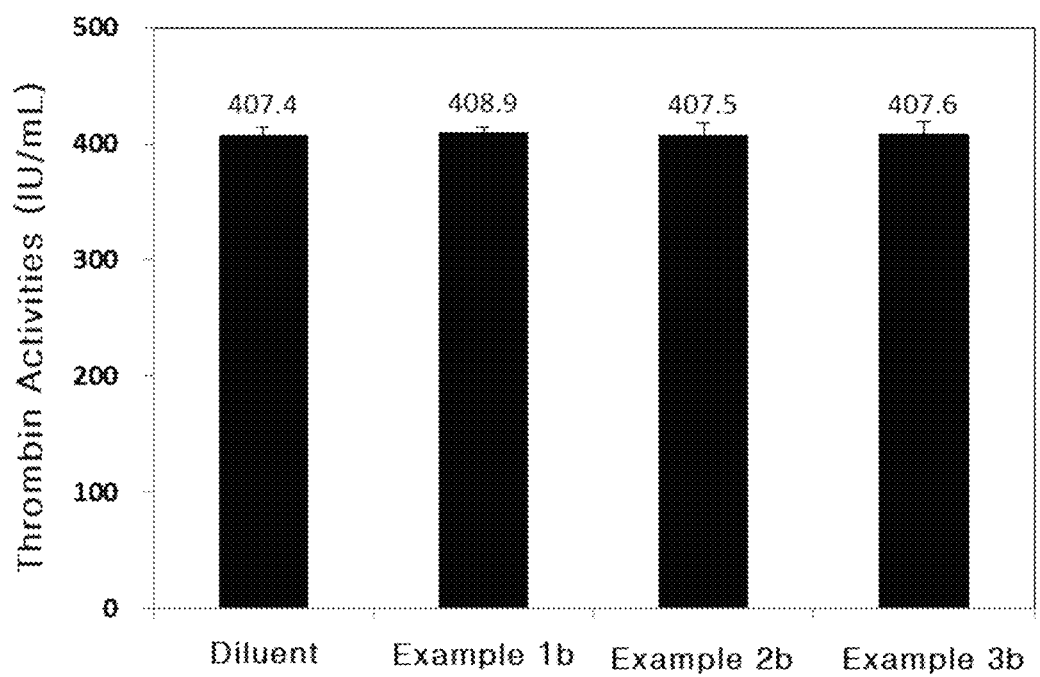

[Fig. 9]
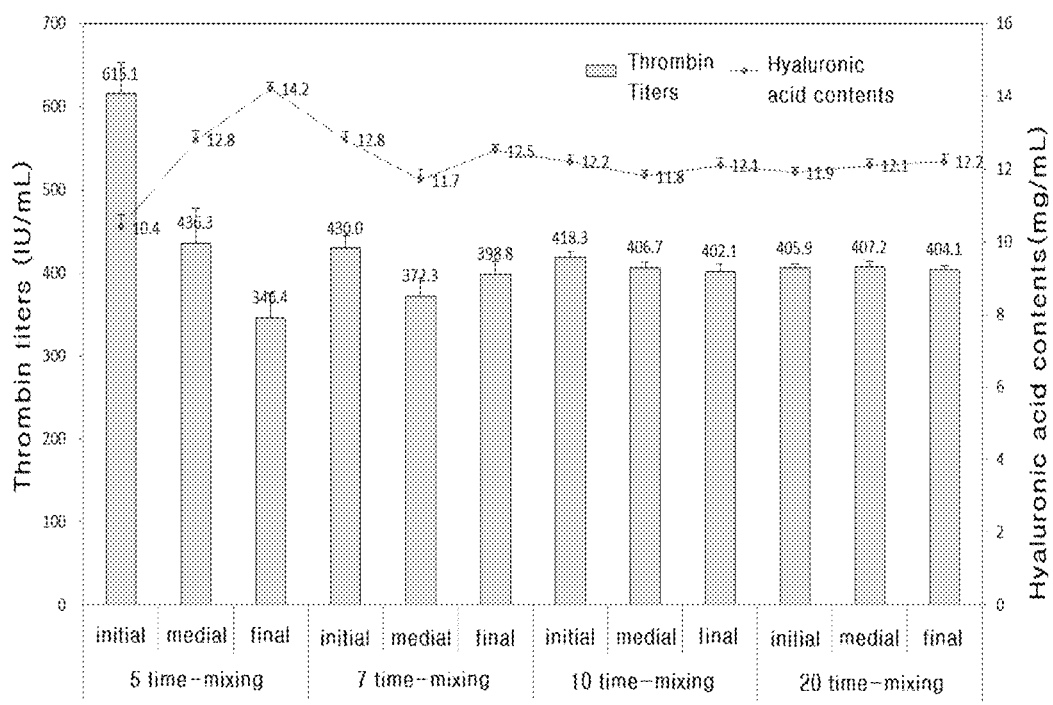
[Fig. 10]
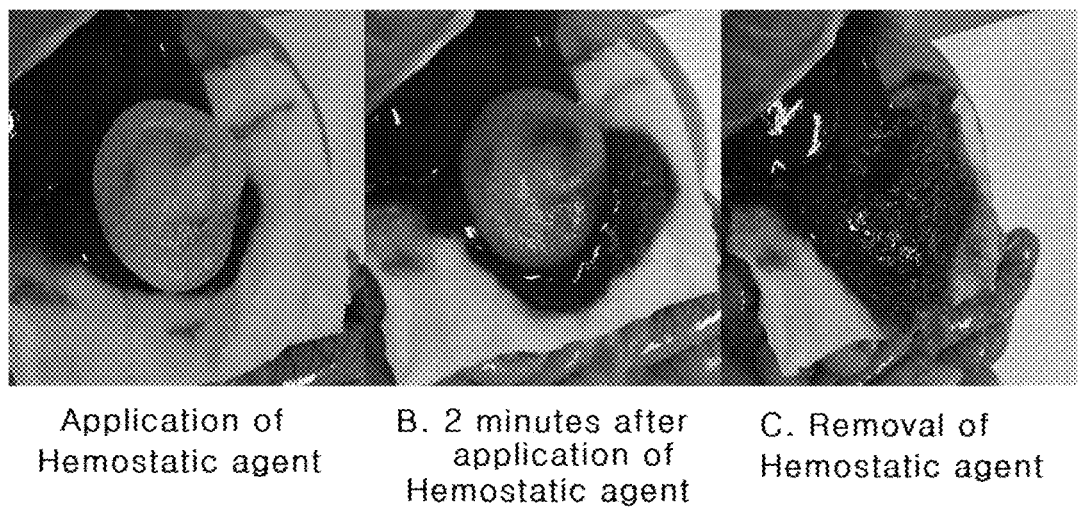
Application of Hemostatic agent | B. 2 minutes after application of Hemostatic agent | C. Removal of Hemostatic agent

[Fig. 11a]
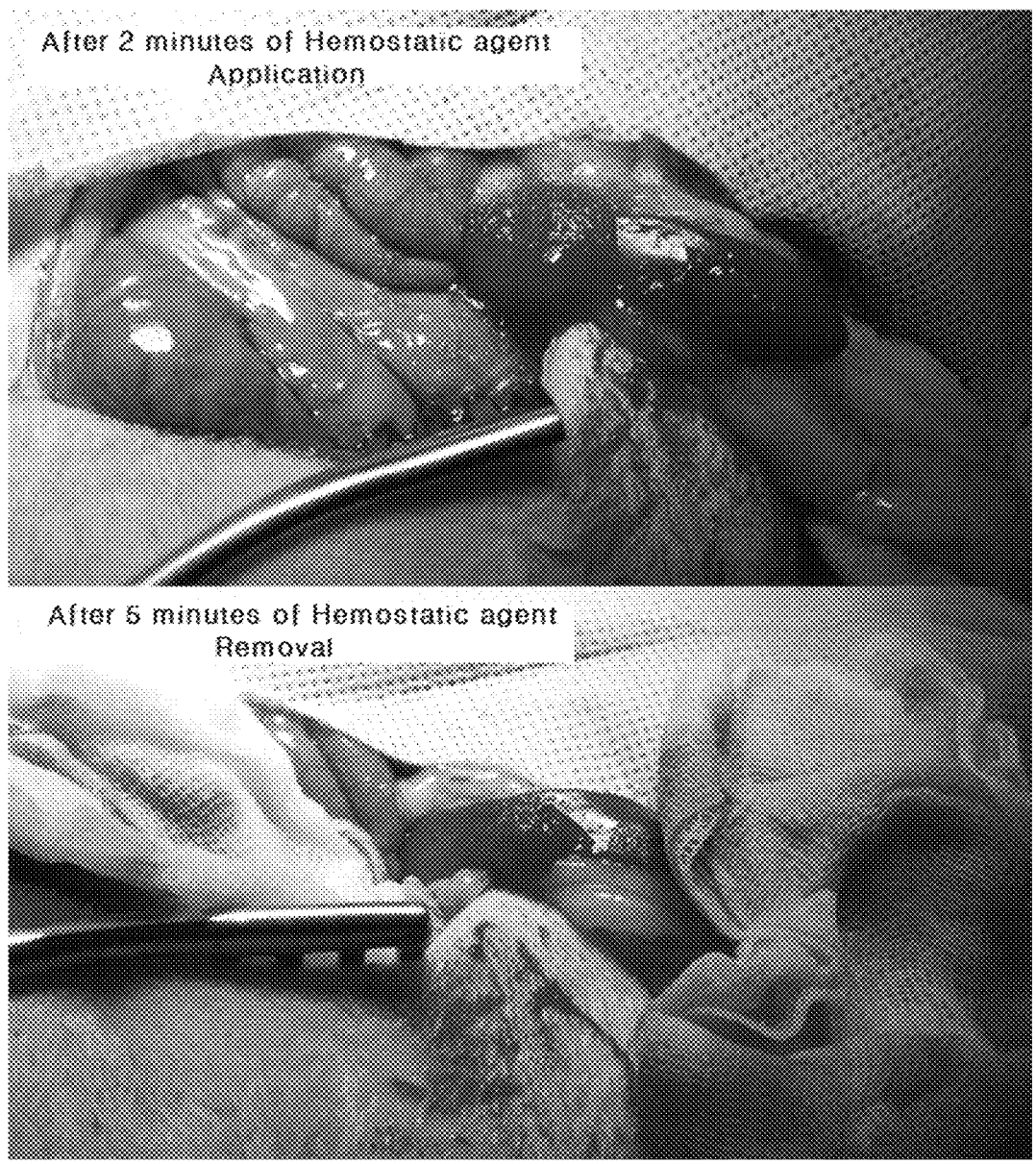

[Fig. 11b]
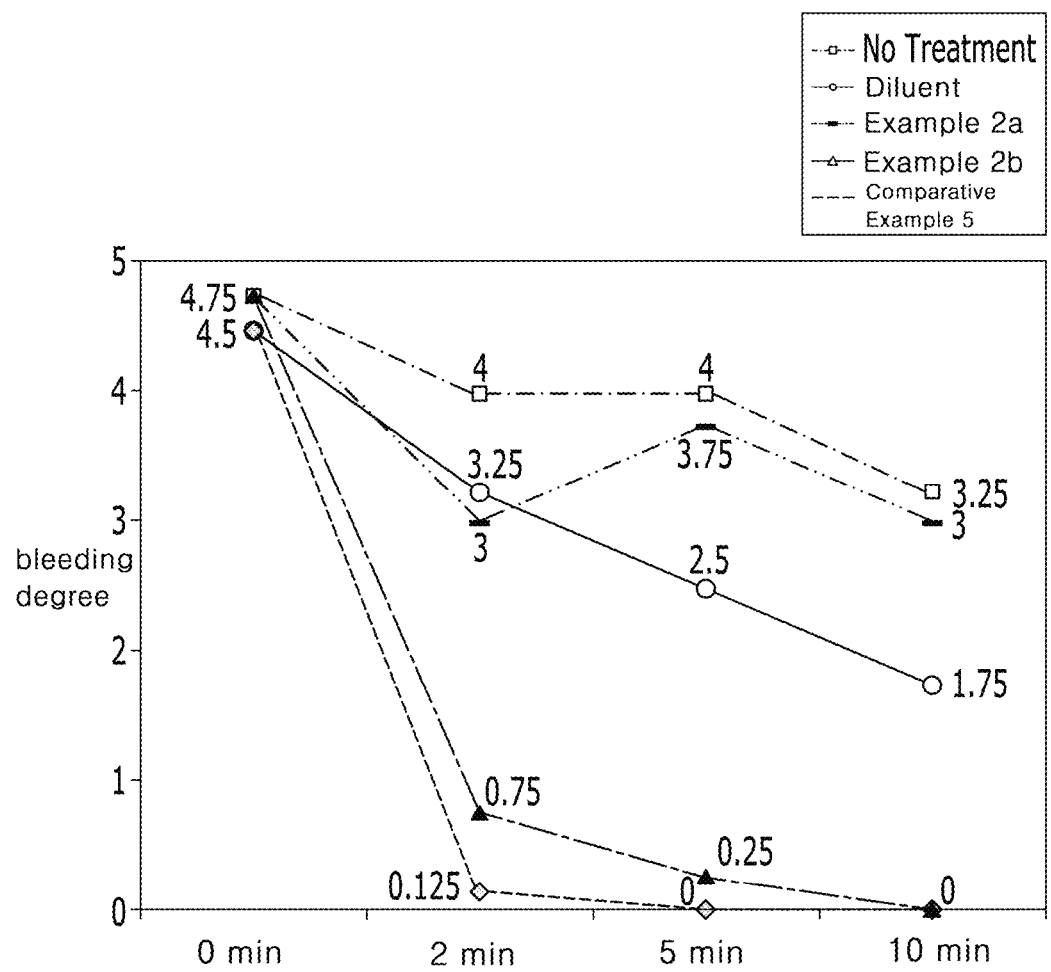

[Fig. 12]
Schematic diagrams comparing hemostatic actions of Example 2 with Com. Example 4
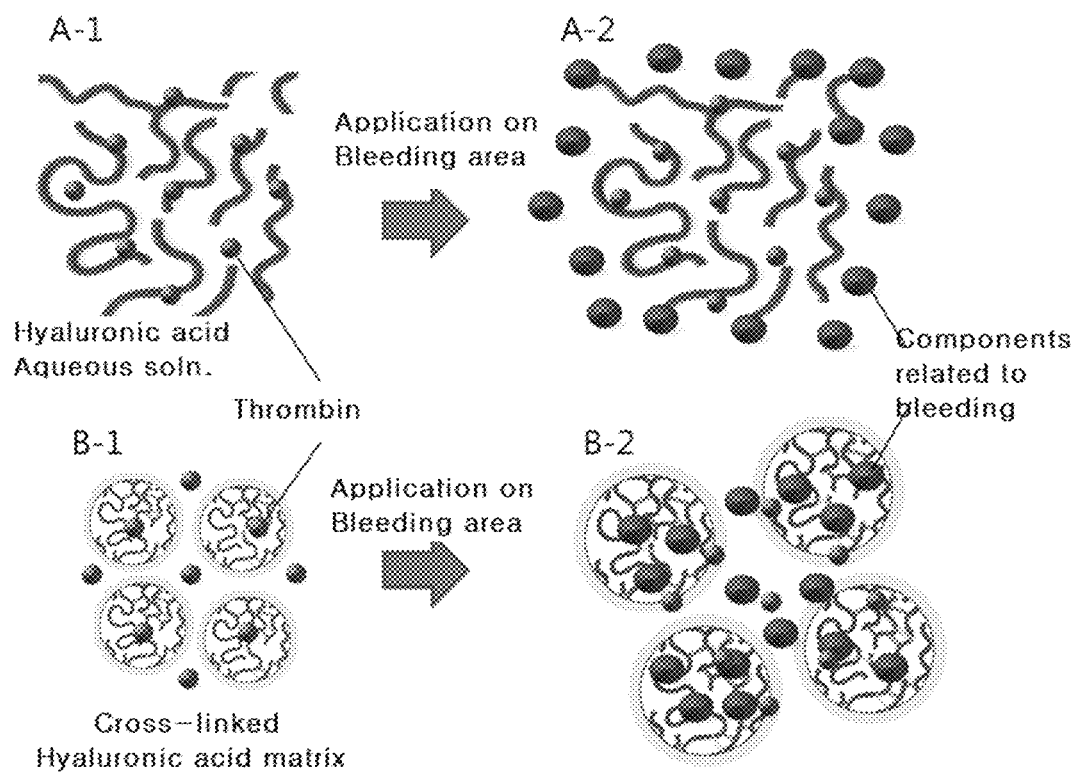
Actual Photographs
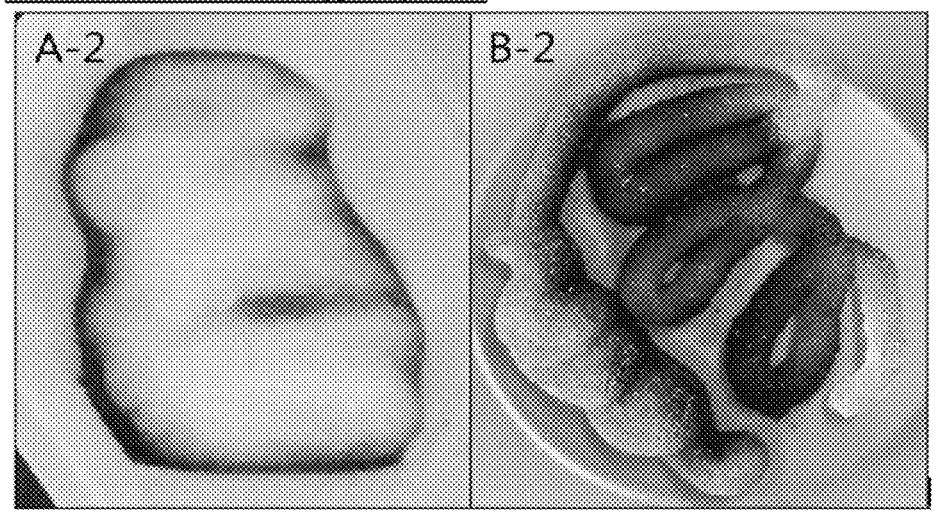

HEMOSTATIC COMPOSITION COMPRISING CROSS-LINKED HYALURONIC ACID DERIVATIVE MATRIX

TECHNICAL FIELD

The present invention relates to a hemostatic composition and a method for preparing thereof, and more specifically, relates to a hemostatic composition comprising a cross-linked hyaluronic acid derivative matrix which is suitable to be used for hemostasis and a method of preparation of such a composition.

BACKGROUND ART

In many areas of surgical operations, bleeding which is not effectively controlled by ligature or general procedures or is uncontrollable can be induced. To stop such severe bleeding, a hemostatic composition can be applied for wounds, and as such a hemostatic composition, it is required to provide a material with strong adhesive force and adequate swelling when applied to human tissues such as wounds.

As an example of a hemostatic composition comprising a biocompatible and biodegradable dry stable granular material, there is Floseal®, and this is a multipurpose hemostatic agent composed of a granular gelatin matrix which swells in a thrombin-containing solution to form a flowable paste.

However, even though the product above has good adhesive force and swelling related to the hemostatic effect, it is comprised of cross-linked and dried gelatin derived from bovine source, so there could be a concern about the safety when applying human surgery.

A hyaluronic acid is one of human body components, and is being used for various purposes such as beverage, beauty, medicines, etc. In particular, it is known that it has possibility to promote regeneration of tissues, and it is harmless to human body, so it has been developed and utilized as a component of an anti-adhesion agent. According to a recent literature, the possibility of hyaluronic acid, as a component of hemostatic matrix, has been suggested through a combination with other hemostatic agent, but as a result of the inventors' test, it was shown that it was difficult to be mixed with a hemostatic component due to localized gelation in the process of hydration, and the viscosity and hygroscopicity after hydration is low, and when mixed composition was applied on wound area, it harmed the wound area due to its excessively high adhesive force, and thus, it is difficult to utilize natural hyaluronic acid as a composition of hemostatic agent.

Under these circumstances, as the result of inventors' intensive studies to overcome the aforementioned problems of the prior art, they have made a hyaluronic acid derivative matrix with appropriate tissue adhesive force and anti-adhesion ability by cross-linking of hyaluronic acid, and have homogenized it to a proper size, and they have developed a hyaluronic acid derivative, which can be easily mixed with other hemostatic components and has appropriate adhesive force for treatment on wound, and thereby they have completed the present invention by confirming that a hemostatic composition comprising such a derivative exhibits an excellent hemostatic effect.

DISCLOSURE

Technical Problem

In order to solve the aforementioned problems, a primary object of the present invention is to provide a hemostatic composition comprising a cross-linked hyaluronic acid derivative matrix.

In addition, another object of the present invention is to provide a method for preparing a hemostatic composition comprising the cross-linked hyaluronic acid derivative matrix.

Advantageous Effects

The hemostatic composition comprising a cross-linked hyaluronic acid derivative matrix according to the present invention has high water-absorbing ability and proper adhesive force for hemostatic purpose. In addition, when applied to a body, it forms an effective barrier which can block leaks from blood vessel. Specifically, the swelling property of the cross-linked hyaluronic acid derivative comprised in the hemostatic composition may increase adhesive force on the bleeding region and make an effective mechanical shield against interstitial adhesion.

The hemostatic composition of the present invention has better adhesive force to tissues than the conventional thrombin solution, and can be completely degraded and absorbed in vivo after a certain period of time. In addition, by using an harmless hyaluronic acid derivative which has appropriate adhesive force comparing to natural sodium hyaluronic acid solution, this new hemostatic composition excludes the risk of side effects which can be caused by using the hemostatic composition made of exogenous materials, as described above.

BRIEF DESCRIPTION OF DRAWINGS

FIG. 1 shows the appearance of the hemostatic composition containing the hyaluronic acid derivative prepared according to the preparation methods of the present invention.

FIG. 2 shows the result of measuring the complex viscosity and tan δ result values in the frequency range of 0.1 Hz to 1 Hz, to investigate rheological characteristics of the hyaluronic acid derivatives prepared as Examples 1a to 3a and Comparative examples 1a, 2a and Comparative example 3a.

FIG. 3 shows the result of absorbing ability of the hyaluronic acid derivatives prepared as Examples 1a to 3a.

FIG. 4 shows the result of confirming the liquid absorptivity of the hemostatic composition containing the hyaluronic acid derivatives prepared as Examples 1b to 3b and the hemostatic composition containing the non-cross-linked hyaluronic acid prepared as Comparative example 4b.

FIG. 5a shows the result of analyzing the particle size of the hemostatic composition containing the hyaluronic acid derivative prepared as Example 2b.

FIG. 5b shows the result of analyzing the particle size of the hemostatic composition containing the hyaluronic acid derivative prepared as Comparative example 5.

FIGS. 6a and b are graphs showing adhesive force of the hyaluronic acid derivatives prepared as Examples 1a to 3a and Comparative examples 1a, 2a and 4a.

FIG. 7a is a photograph showing the appearance of the hemostatic compositions prepared as hemostatic Example 2b and Comparative examples 2b and 4b on flat glass plate.

FIG. 7b is a graph showing the result of the comparative test of adhesive force of the hemostatic compositions prepared in hemostatic Example 2b and Comparative examples 2b and 4b as the distance of the sample movement.

FIG. 8 shows the result of comparing the thrombin activities of the thrombin containing diluent used in the preparation of the hemostatic composition and the hemostatic compositions prepared as Examples 1b to 3b.

FIG. 9 shows changes in the hyaluronic acid contents and thrombin titers according to the mixing times.

FIG. 10 shows the result of confirming the hemostatic ability of Example 3b in SD rat liver lesion.

FIG. 11a is a photograph of the test result confirming the hemostatic effect of the hemostatic composition prepared as Example 3b in rabbit spleen lesion.

FIG. 11b is a photograph showing the hemostatic effect of the hemostatic composition prepared in Example 1-3 in rabbit spleen lesion as a degree of bleeding.

FIG. 12 shows the schematic diagrams comparing hemostatic actions of the hemostatic composition of the present invention and non-cross-linked sodium hyaluronic acid. Bottom part shows actual photographs of the hemostatic composition according to the present invention.

BEST MODE

As one aspect to achieve the aforementioned objects, the present invention relates to a hemostatic composition comprising a cross-linked hyaluronic acid derivative matrix.

The hemostatic composition of the present invention is a component for hemostasis, and comprises a cross-linked hyaluronic acid derivative matrix having appropriate hygroscopicity and viscosity. As specific one aspect, the cross-linked hyaluronic acid derivative may be obtained by cross-linking hyaluronic acid (HA) or its salt form, using an epoxide cross-linking agent having two or more of epoxide groups. The cross-linked hyaluronic acid can maintain natural hygroscopicity of hyaluronic acid and form a matrix through cross-linking between hyaluronic acid, and the hygroscopicity and viscosity for additional solution are increased while the adhesive force is reduced, and therefore these features enable smooth mixing with solution comprising a hemostatic component.

The hyaluronic acid is a natural heteropolysaccharide consisting of alternating residues of D-glucuronic acid and N-acetyl-D-glucosamine, and a hyaluronic acid derivative matrix can be produced by cross-linking with epoxide agents. In the present invention, in addition to the hyaluronic acid, its salt form may be also used.

The epoxide cross-linking agent, specifically, may be 1,4-butanediol diglycidyl ether (BDDE), ethylene glycol diglycidyl ether (EGDGE), 1,6-hexanediol diglycidyl ether, propylene glycol diglycidyl ether, poly(propylene glycol) diglycidyl ether, poly(tetramethylene glycol) diglycidyl ether, neopentyl glycol diglycidyl ether, polyglycerol polyglycidyl ether, diglycerol polyglycidyl ether, glycerol polyglycidyl ether, trimethylpropane polyglycidyl ether, 1,2-(bis(2,3-epoxypropoxy)ethylene, pentaerythritol polyglycidyl ether or sorbitol polyglycidyl ether, and more specifically, may be 1,4-butanediol diglycidyl ether (BDDE).

The complex viscosity of the cross-linked hyaluronic acid derivative matrix of the present invention is 10 to 500,000 Pa·s at 1 Hz (25° C.) (Rotational Rheometer (TA instrument Ltd., DHR-1), Temperature: 25° C.).

In addition, the cross-linked hyaluronic acid derivative matrix has advantages of having the higher water absorbing ability (FIG. 3) and greater swelling degree than natural hyaluronic acid. Specifically, the swelling degree of the cross-linked hyaluronic acid derivative matrix in the gel state is 200% to 1,500%, and in case of the dried powder (105° C., 6 hours), the swelling degree is 300% to 75,000%.

In addition, the cross-linked hyaluronic acid derivative matrix is cross-linked according to the unique synthesis conditions of the present invention, so the molecular binding between hyaluronic acid is increased and the viscoelasticity is increased (FIG. 2) and it has the appropriate adhesive force to a living tissue. Further, since the cross-linked part is not degraded by internal hyaluronidase, it has properties of enhanced stability inside body while little risk of toxicity. In addition, it can form a physical barrier on its applied area for a certain time after completing the hemostatic role.

Due to the aforementioned characteristics, the composition according to the present invention is particularly useful to provide the hemostatic effect on the bleeding region including surgical bleeding region, external injury bleeding region, etc., and therefore it can be easily and conveniently used for medical uses, specifically, in use for arresting bleeding when various bleeding is occurred such as surgical operations, etc.

As another aspect, the present invention relates to a method for preparing the hemostatic composition comprising the cross-linked hyaluronic acid derivative matrix. Specifically, the method of preparation may comprise i) a step of reacting hyaluronic acid and an epoxide cross-linking agent which are dissolved in a basic aqueous solution to prepare a cross-linked hyaluronic acid derivative; and ii) a step of homogenizing the cross-linked hyaluronic acid derivative to prepare it to an appropriate size.

Preferably, in the method of preparation of the hyaluronic acid derivative according to the present invention, a hyaluronic acid derivative prepared by homogenizing products obtained by reacting an epoxide cross-linking agent comprising two or more of epoxide groups to hyaluronic acid (HA) is prepared.

In the method of preparation of the present invention, hyaluronic acid (HA) or its salt form may be used, and the salt forms comprises at least one or more selected from the group consisting of sodium hyaluronic acid, potassium hyaluronic acid, calcium hyaluronic acid, magnesium hyaluronic acid, zinc hyaluronic acid, cobalt hyaluronic acid and tetrabutylammonium hyaluronic acid.

In the method of preparation, in the i) step, as the basic aqueous solution used for ionization for cross-linking reaction of hyaluronic acid, NaOH, KOH, ammonia aqueous solution, etc. may be used. In addition, the concentration of the hyaluronic acid dissolved in the basic aqueous solution is preferably 50 to 200 mg/mL, and the cross-linking ratio of the epoxide cross-linking agent (for example, BDDE) varies, depending on the concentration of the hyaluronic acid dissolved in the basic aqueous solution. As one example, when the concentration of the hyaluronic acid dissolved in the basic aqueous solution is 20 mg/mL, the input of BDDE as the epoxide cross-linking agent is 2% to 50% (the ratio of the volume of the epoxide cross-linking agent to the weight of the basic aqueous solution in which the hyaluronic acid is dissolved (v/w)), and when the concentration of the hyaluronic acid dissolved in the basic aqueous solution is 200 mg/mL, the input of BDDE is 0.01% to 5% (the ratio of the volume of the epoxide cross-linking agent to the weight of the basic aqueous solution in which the hyaluronic acid is dissolved (v/w)). In addition, in the i) step, the reaction temperature is 4 to 80 degree Celsius, and the reaction time is 12 hours to 48 hours, and the reaction pressure is 0.5 atm to 2 atm, preferably atmospheric pressure.

The epoxide cross-linking agent of the i) step may be selected from 1,4-butanediol diglycidyl ether (BDDE), ethylene glycol diglycidyl ether (EGDGE), 1,6-hexanediol diglycidyl ether, propylene glycol diglycidyl ether, poly (propylene glycol) diglycidyl ether, poly(tetramethylene glycol) diglycidyl ether, neopentyl glycol diglycidyl ether, polyglycerol polyglycidyl ether, diglycerol polyglycidyl ether, glycerol polyglycidyl ether, trimethylpropane polyglycidyl ether, 1,2-(bis(2,3-epoxypropoxy)ethylene, pentaerythritol polyglycidyl ether or sorbitol polyglycidyl ether, and more specifically, 1,4-butanediol diglycidyl ether (BDDE) may be used.

As additional one aspect, the hyaluronic acid derivative prepared in the i) step may be washed by physiological saline solution, etc. before being processed in the ii) step. In addition to the washing step, the hyaluronic acid derivative prepared in the i) step may be isolated and/or purified by methods known in the art, for example, distillation (under the atmospheric pressure or reduced pressure), recrystallization, column chromatography, ion-exchange chromatography, gel chromatography, affinity chromatography, thin-layer chromatography, phase separation, solvent extraction or dialysis.

Moreover, the ii) step is a step of homogenizing the cross-linked hyaluronic acid derivative prepared in the i) step to prepare it in a gel form. The method of homogenizing may be performed by conventional homogenizing methods, for example, a blade homogenizing or compression homogenizing method, and it may be performed at least 3 times for homogeneous particles, but it is not limited thereto.

In particular, the size and shape of the hyaluronic acid derivative are not particularly limited, and its size and shape may be varied according to the medically applied range, and the size of the hydrogel ground in the ii) step is preferably 10 to 2000 μm, and more specifically 200 μm to 800 μm, but it may be ground into other sizes and used, if necessary.

The hyaluronic acid derivative prepared through the i) and ii) steps may be used as sterilized under the high temperature and high pressure. Thus, as additional one aspect, the method of preparation according to the present invention may further comprise a step of sterilizing the hyaluronic acid derivative prepared in the ii) step.

The complex viscosity of the hydrogel prepared according to the method of preparation of a hyaluronic acid derivative of the present invention is 10 to 500,000 Pa·s at 1 Hz (25° C.), and the swelling degree is 200% to 1,500%. In addition, in case that the hyaluronic acid derivative is in the form of powder, the swelling degree reaches 75,000%.

As other aspect, the present invention relates to a kit for hemostasis comprising the hemostatic composition according to the present invention and a pharmaceutically acceptable diluent.

Specifically, the kit for hemostasis according to the present invention may comprise a diluent comprising a coagulation-inducing agent together with the hemostatic composition comprising a hyaluronic acid derivative. Preferably, in the kit for hemostasis, the hemostatic composition comprising a hyaluronic acid derivative: the diluent comprising a coagulation-inducing agent may be comprised at the weight ratio of 2:8 to 9:1.

The coagulation-inducing agent comprised in the diluent used for the kit according to the present invention is a material which induces coagulation of blood, and for example, it may be one or more selected from the group consisting of thrombin, any of snake venom components, platelet activator, thrombin receptor-activating peptide, fibrinogen precipitator, aprotinin and factor VIII, but not limited thereto. Preferably, it is thrombin. Thrombin may be induced from any thrombin agent suitable for use in humans (i.e., pharmaceutically acceptable). The appropriate source of thrombin includes human and bovine blood, plasma or serum (when no immunological rejection is anticipated, thrombin of other animal sources of supply may be applied), and thrombin of recombinant origin (for example, human recombinant thrombin) and autologous human thrombin may be preferable for some applications, and this applies equally to other coagulation-inducing agents.

The pharmaceutically acceptable diluent is used at an amount to achieve a preferable final-concentration with its ready-to-use composition. Such a diluent comprising a coagulation-inducing agent may contain other useful components, for example, an ion, a buffer solution, an excipient, a stabilizer, etc., in addition to the aforementioned coagulation-inducing agent. The preferable salt is NaCl and/or $CaCl_2$, and the preferable stabilizer is glycine, and all of them are used at a general amount and concentration, applied for the coagulation-inducing agent including thrombin (for example, 0.5 to 1.5% NaCl (for example, 0.9%) and/or 20 to 80 mM $CaCl_2$ (for example, 40 mM)). In additional embodiments, the diluent may also comprise a buffer solution or buffer system, to buffer at the pH of the reconstituted dried composition, preferably at a pH of 3.0 to 10.0, more preferably at a pH of 6.5 to 8.5. For example, the diluent may comprise injectable grade water, and—independently of each other—100 to 10,000 IU/vial thrombin (preferably 1,000 to 5,000 IU/vial), 50 to 200 mM NaCl (preferably 100 to 200 mM), 10 to 80 mM $CaCl_2$ (preferably 30 to 50 mM) and 5 to 100 mg/mL glycine (preferably 5 to 20 mg/mL). As specific one aspect, the diluent comprising a coagulation-inducing agent may be comprised in the kit as an aqueous solution and a material selected from the group consisting of a coagulation-inducing agent, NaCl, $CaCl_2$, albumin and glycine are separately isolated (for example, a form contained in the vial as lyophilized), and when the kit is used, the material selected from the group consisting of a coagulation-inducing agent, NaCl, $CaCl_2$, albumin and glycine may be dissolved in the aqueous solution.

In other embodiment, the diluent comprising a coagulation-inducing agent may contain sodium acetate in small quantity, specifically 1 to 50 mM, preferably 10 to 30 mM. In addition, the diluent comprising a coagulation-inducing agent may contain less than 100 g/l of mannitol, preferably less than 50 g/l, and may contain less than 200 g/l of lactose, preferably less than 100 g/l. Preferably, the diluent comprising a coagulation-inducing agent may not necessarily contain sodium acetate, mannitol and lactose. Specifically, by comprising glycine in the above range, glycine alone can maintain the lyophilized cake form of the coagulation-inducing agent including thrombin and also stabilizes the titer of the coagulation-inducing agent, without sodium acetate, mannitol or lactose.

According to a preferable embodiment, when the diluent comprises thrombin as a coagulation-inducing agent, it comprises preferably 10 to 10,000 I.U. thrombin/ml, particularly 250 to 5,000 I.U. thrombin/ml. Preferably, such a ready-to-use form of kit for hemostasis contains 10 to 100,000 international unit (I.U.) thrombin, more preferably 500 to 20,000 I.U., particularly 1,000 to 10,000 I.U. In preferable one aspect, the kit for hemostasis according to the present invention may be in a form of prefilled syringe. The term "prefilled syringe" is one prepared by filling a certain amount of preparation for injection as it is into a syringe, and means ready-to-use, that is, it can be used immediately without requiring weighing of drugs and filling in a syringe, etc. in use.

In specific one embodiment, the kit for hemostasis according to the present invention may be prepared by connecting a prefilled syringe filled with a hemostatic composition comprising a hyaluronic acid derivative according to the present invention to a connector, and connecting a syringe filled with a diluent comprising a coagulation-inducing agent to the other terminal of the connector to inject it, thereby hydrating a hemostatic composition comprising a cross-linked hyaluronic acid derivative matrix. In order to obtain homogeneous products, reciprocal injection may be repeated between hyaluronic acid derivative syringe and coagulation-inducing agent-containing diluent syringe, and they may be prepared by reciprocating preferably 5 times or more, more preferably about 10 times.

Such a kit for hemostasis according to the present invention comprises the hemostatic composition comprising a hyaluronic acid derivative and a diluent comprising thrombin as a coagulation-inducing agent in combination, thereby exhibiting an excellent hemostatic effect comparing to thrombin alone (See FIG. 10, etc.).

MODE FOR INVENTION

Hereinafter, the present invention will be described in more detail with reference to the following examples. However, the description of the following examples is intended only to illustrate specific embodiments of the present invention and is not intended to limit or limitingly interpret the scope of the invention to the contents described therein.

Example 1-3. Preparation of Hyaluronic Acid Derivatives for Hemostatic Compositions A. Preparation of Cross-Linked Hyaluronic Acid Derivative Matrices After 1 g of sodium hyaluronic acid was prepared in each of 3 reactors, it was added to reach the final weight of 10.0 g (Example 1a), 8.3 g (Example 2a), and 7.1 g (Example 3a) using 0.25 N NaOH solution. To the completely dissolved solution, 1,4-butanediol diglycidyl ether (BDDE) of 70 uL (Example 1a), 60 uL (Example 2a) and 50 uL (Example 3a) was added, and then they were mixed. The mixed solutions were put in a constant-temperature water bath and reacted at 30° C. for 18 hours, and then washed with a buffer solution to remove non-reacted materials. The prepared gels were homogenized 3 times or more by a compression method to control the particle size, and then they were sterilized at 121° C. for 15 minutes. 3.0 g of the prepared hyaluronic acid derivatives were aseptically weighed in 5 ml syringes, and then terminal-sterilized at 127° C. for 2 minutes to prepare hyaluronic acid derivative prefilled syringes (Example 1a, 2a, 3a).

B. Preparation of Diluent

Thrombin 5,000 IU, glycine, sodium chloride, calcium chloride raw materials per 1 vial were added, and then dissolved by adding a proper amount of water for injection. The dissolved solution was aseptically filtered and filled in vials, followed by lyophilization. The lyophilized powder was completely dissolved with 0.9% physiological saline injection just before being used in a bleeding region and used.

C. Preparation of Hemostatic Compositions Comprising a Cross-Linked Hyaluronic Acid Derivative Matrix The prefilled syringes filled with hyaluronic acid derivatives (Examples 1a, 2a, 3a) were connected to a connector, and the hyaluronic acid derivatives were hydrated by using the diluent comprising thrombin. In order to obtain homogeneous products, a cylinder was reciprocated between hyaluronic acid derivative syringe and thrombin-containing diluent syringe, then at least 10 times of reciprocal mixing were conducted to prepare hemostatic compositions (Examples 1b, 2b, 3b). The appearance of the prepared hemostatic compositions containing a hyaluronic acid derivative is shown in FIG. 1.

Example 4. Rheological Characteristics of Hyaluronic Acid Derivatives

To investigate rheological characteristics of the hyaluronic acid derivatives prepared as Examples 1a to 3a, and an anti-adhesion agent of B company (Comparative example 1a), and a cross-linked hyaluronic acid filler of G company (Comparative example 2a) and a cross-linked hyaluronic acid filler of L company (Comparative example 3a), which were commercially available and contained hyaluronic acid, rotational rheometer test was conducted. The complex viscosity and tan δ result values in the frequency range of 0.1 Hz to 1 Hz were shown in FIG. 2.

By FIG. 2 and Table 1, Examples 1a to 3a shows higher complex viscosity values than Comparative examples 1a to 3a. Through this, it can be seen that the hyaluronic acid derivatives of the present invention (Examples 1a to 3a) have higher viscosity than Comparative examples 1a to 3a, and they formed a structure with high structural stability.

TABLE 1

| | Frequency (1 Hz) Complex viscosity (Pa · s) |
|---|---|
| Example 1a | 4,313 |
| Example 2a | 28,460 |
| Example 3a | 670 |
| Comparative example 1a | 0.543 |
| Comparative example 2a | 91 |
| Comparative example 3a | 66 |

Example 5. Swelling Degree of Hyaluronic Acid Derivatives

After 100 ml of physiological saline solution was added to 3.0 mL of the hyaluronic acid derivatives prepared as Examples 1a to 3a, they were stirred for 10 minutes. After keeping them at 37° C. for 1 hour, the unabsorbed physiological saline solution was removed, and then the volume of the solution absorbed to the hyaluronic acid derivatives was confirmed.

FIG. 3 is the result of the swelling degree of the hyaluronic acid derivatives prepared as Examples 1a to 3a, and the swelling degree of Example 1a is 706%, and the swelling degree of Example 2a is 607%, and the swelling degree of Example 3a is 409%. The hyaluronic acid derivatives of the present invention (Examples 1a to 3a) exhibited the absorbing ability to absorb moisture of 4 to 7 times of their volumes or more.

Example 6. Comparison of Absorbing Ability of Hyaluronic Acid Derivative-Containing Hemostatic Compositions and Non-Cross-Linked Hyaluronic Acid-Containing Hemostatic Composition Comparative example 4: after dissolving 1,000 mg of sodium hyaluronic acid in a buffer solution at a concentration of 20% by weight, the solution was weighed in a 5 ml syringe and terminal-sterilized at 127° C. for 2 minutes (Comparative example 4a). The preparation process of a hemostatic composition using a diluent was conducted as same as Examples 1b to 3b to prepare the final composition (Comparative example 4b).

FIG. 4 is the result of confirming the liquid absorptivity of the hyaluronic acid derivative-containing hemostatic compositions prepared as Examples 1b to 3b and the composition prepared in Comparative example 4b. To confirm the absorptivity, 5.0 g of the test article was applied to a dish, and then 1.0 mL of physiological saline solution with blue dye was poured on the test article to observe the absorption of the liquid.

By FIG. 4, it was illustrated the phenomenon that the liquid was absorbed between particles faster in the hemostatic compositions comprising a hyaluronic acid derivative, Examples 1b to 3b, compared to Comparative example 4b.

Example 7. Analysis of Particle Size of Hemostatic Compositions Comprising a Hyaluronic Acid Derivative To measure the particle size and distribution of the hemostatic composition comprising the hyaluronic acid derivative of Example 2b, 3 g of each sample was diluted with 15 mL distilled water and the particles between 0.375 um to 2000 um were counted using Beckman Coulter LS Particle Size Analyzer. The result was shown in FIG. 5a. FIG. 5b is the result of analysis of the particle size of the granule form of hemostatic agent, Floseal® (Comparative example 5).

By FIGS. 5a and b, it was confirmed that the average particle size of Example 2b was 638.5 um and the average particle size of Comparative example 5 was 462.8 um, and the hemostatic composition of Example 2b exhibited even particle distribution, compared to Comparative example 5.

Example 8. Confirmation Test of Adhesive Force of Hyaluronic Acid Derivatives

To measure tack values, each sample of Comparative example 1a, Comparative example 2a, Comparative example 4a and Examples 1a to 3a was loaded on a plate of the rheometer, and then rotated at a shear rate of 0.1 for 10 seconds, and the normal force values when geometry was separated at a rate of 0.1 mm/s were measured.

FIGS. 6a and b show the normal force (N) values according to GAP (mm) for each sample, and comparing the maximum normal forces (N) shown in this figure, Examples 1a to 3a of the present invention exhibited higher normal force values than Comparative example 1a (anti-adhesion agent of B company), Comparative example 2a (cross-linked hyaluronic acid filler product of G company) and Comparative example 4a (non-cross-linked hyaluronic acid solution). In other words, Examples of the present invention exhibited higher adhesive force than Comparative examples.

Example 9. Comparison Test of Adhesive Force of Hyaluronic Acid Derivatives

To measure the adhesive force of hemostatic compositions, the sample 3 g of Comparative example 2 was prepared by using the diluent as same as Example 2b (Comparative example 2b).

About 0.5 mL of Comparative example 4b, Comparative example 2b and Example 2b samples were dropped on a flat glass plate and a 30 degrees inclined glass plated and had been kept for 5 minutes at ambient conditions, and then the movement length of each sample was measured. The moving distance of each sample was calculated by the difference between the length of the sample on the 30 degrees inclined glass plate and the length of the sample on the flat glass plate.

FIGS. 7a and b illustrate the appearance of Comparative example 4b, Comparative example 2b and Example 2b samples loaded on the flat glass plate, and Example 2b exhibited higher adhesive force than Comparative example 2b and Comparative example 4b.

Example 10. Effect of Hyaluronic Acid Derivatives on Thrombin Activity

The thrombin activity was tested according to the thrombin quantitation method of Korean Pharmacopoeia 11th edition. The detailed operation method is as follows.

The thrombin standard preparation was dissolved in injectable physiological saline at 25 degree Celsius to produce 4 kinds of standard solutions containing 4.0, 5.0, 6.2 and 7.5 units in 1 mL, and then 0.10 mL of each was added to a test tube. 0.90 mL of fibrinogen solution prewarmed at the same temperature was added to the test tube in which has thrombin standard solution using micropipette, and at the same time, a timer was activated and it was shaken gently, and the time until the first fibrin coagulation occurrence was measured. It was measured 5 times respectively with 4 kinds of standard solutions, and their average value was calculated.

The measurement for the test article was performed by the same method at the same temperature as above. The test article was dissolved in the injectable physiological saline and a solution containing 5 units in 1 mL was made, and by using 0.10 mL of it, the above operation was repeated 5 times to measure the coagulation time and calculate the average value. By unit on the horizontal axis of a log-log graph and coagulation time on the vertical axis, a calibration curve was prepared by taking the average value of coagulation times by the 4 kinds of standard solutions on the graph. The unit numbers U—were calculated by applying the average value of the coagulation times of the test solutions on the calibration curve above.

FIG. 8 is the result of comparing the thrombin activity of thrombin solution which was diluted only in the diluent and hemostatic compositions prepared as Examples 1b to 3b. The thrombin titer of the diluent without a hyaluronic acid derivative and the thrombin titer of the hemostatic compositions comprising a hyaluronic acid derivative were similar. As a result, it was confirmed that the hyaluronic acid derivative did not affect the activity of thrombin.

Example 11. Effect of Hyaluronic Acid Derivatives on Thrombin Activity

To check the changes of the hyaluronic acid content and thrombin titer by the mixing times in the process of preparing the hemostatic composition, 3.0 g of the hyaluronic acid derivative prepared in Example 2a was filled to a prefilled syringe, and then the hyaluronic acid derivative was hydrated by using a diluent comprising 1,000 IU/mL thrombin. FIG. 9 shows the test result of the thrombin titer and hyaluronic acid content of samples in which the hydration process was progressed by reciprocating 5 times, 7 times, 10 times and 20 times respectively.

By FIG. 9, it was confirmed that the mixing between the hyaluronic acid derivative and the diluent had to proceed at least 10 times or more to obtain a homogeneous hemostatic composition.

Example 12. Hemostatic Effect Test in Rat Model

For the hemostatic effect in liver lesions of SD rat, the preparation of Example 2b was tested. For the animal model, the midline laparotomy of rat was performed and then by using a scalpel, the core tissue was removed by approximately a width of 1 cm, a length of 1 cm, and a depth of 0.2 cm. Using an application device tip, to the bleeding wound, approximately 1.0 mL of assigned test article was locally applied to lesions. In 2 minutes after applying the test article, the applied test article was removed and the bleeding degree was observed at 1, 2, 5 and 10 minutes after its removal. The result was illustrated in FIG. 10.

FIG. 10 is the result of confirming the hemostatic effect of Example 2b in SD rat liver lesions. It was observed that the hemostatic composition prepared as Example 2b absorbed blood as time passed. After 2 minutes, when the hemostatic agent was removed with a wet gauze, the hemostasis in the wound tissue was observed.

Example 13. Hemostatic Effect Test in Rabbit Model

To confirm the hemostatic effect in spleen lesions of a rabbit, bleeding was induced by puncturing 4 mm in the spleen of the rabbit. Approximately 1.0 mL of assigned test articles were applied locally to the wound, and then they were pressed with fingers for 5 seconds with a wet gauze to aid the approach of the test article to the applied area. The wet gauze was removed after 2 minutes, and the test article was washed by using physiological saline solution. The bleeding degree was observed every 2, 5 and 10 minutes after washing, and the result was shown in FIGS. 11a and b.

By FIGS. 11a and b, the excellent tissue adhesive force and blood absorbing ability of the hemostatic composition prepared as Example 2b were confirmed. Two minutes after its removal, saturation with blood from the bleeding tissue was observed in Example 2b, and hemostasis was achieved without leaking out of the product. In addition, even after removing the hemostatic agent using physiological saline solution, there was no rebleeding and the clotted blood was observed.

The invention claimed is:

1. A kit for hemostasis comprising a matrix which is cross-linked hyaluronic acid derivative produced by cross-linking hyaluronic acid or its salt, and a diluent comprising a coagulation-inducing agent one or more selected from the group consisting of thrombin and fibrinogen,
   wherein the complex viscosity of the matrix is 670 to 28,460 Pa·s at 1 Hz (25° C.).

2. The kit for hemostasis according to claim 1, wherein the hyaluronic acid derivative has a particle size of 10 to 2000 μm in size.

3. The kit for hemostasis according to claim 1, which is intended to be used in treatment of injury selected from the group consisting of wounds, bleeding, damaged tissue, bleeding tissue and/or bone defect.

4. The kit according to claim 1, wherein the diluent comprising the coagulation-inducing agent comprises 10 to 10,000 I.U./ml of thrombin.

5. The kit according to claim 1, wherein the diluent comprising the coagulation-inducing agent further comprises a material selected from the group consisting of NaCl, $CaCl_2$ and glycine.

6. The kit according to claim 1, wherein the diluent comprising the coagulation-inducing agent comprises a buffer solution or buffer system at a pH of 3.0 to 10.0.

7. The kit according to claim 1, wherein the matrix is comprised in the form of a prefilled syringe.

8. A method of preparation of the hemostatic composition according to claim 1, comprising
   i) a step of reacting hyaluronic acid and an epoxide cross-linking agent which are dissolved in a basic aqueous solution to prepare a cross-linked hyaluronic acid derivative; and
   ii) a step of homogenizing the cross-linked hyaluronic acid derivative.

9. The method of preparation according to claim 8, wherein the concentration of the hyaluronic acid dissolved in the basic aqueous solution is 20 to 200 mg/m L.

10. The method of preparation according to claim 8, wherein the concentration of the hyaluronic acid dissolved in the basic aqueous solution is 20 to 200 mg/mL, and the input of the epoxide cross-linking agent is 0.01 to 50%(v/w).

11. The method of preparation according to claim 8, further comprising a step of sterilizing the hyaluronic acid derivative prepared in the step ii).

* * * * *